United States Patent [19]

Flynn et al.

[11] Patent Number: 4,889,656

[45] Date of Patent: Dec. 26, 1989

[54] PERFLUORO(CYCLOALIPHATIC METHYLENEOXYALKYLENE) CARBONYL FLUORIDES AND DERIVATIVES THEREOF

[75] Inventors: Richard M. Flynn; Patricia M. Savu, both of St. Paul, Minn.

[73] Assignee: Minnesota Mining and Manufacturing Company, St Paul, Minn.

[21] Appl. No.: 116,259

[22] Filed: Oct. 30, 1987

[51] Int. Cl.$^4$ .............................................. B01F 17/30
[52] U.S. Cl. ..................................... 252/356; 544/162; 544/171; 544/177; 546/184; 546/248; 556/1; 562/501; 562/507; 562/849; 564/142
[58] Field of Search ........... 260/501.16, 543 F, 544 F; 544/162, 171, 177; 546/248, 184; 556/1; 558/44, 53; 562/507, 501; 564/142; 252/351, 356

[56] References Cited

U.S. PATENT DOCUMENTS

| | | | |
|---|---|---|---|
| 2,593,737 | 4/1952 | Diesslin et al. | 260/514 |
| 3,250,808 | 5/1966 | Moore et al. | 260/535 |
| 3,271,341 | 9/1966 | Garrison | 260/29.6 |
| 3,409,647 | 11/1968 | Pittman et al. | 260/501.16 |
| 3,600,433 | 8/1971 | Holland et al. | 260/486 R |
| 3,699,156 | 10/1972 | Holland et al. | 260/486 H |
| 3,891,591 | 6/1975 | Chang et al. | 525/207 |
| 3,892,668 | 7/1975 | Chiu | 252/356 |
| 3,996,206 | 12/1976 | Parker et al. | 252/356 |
| 4,035,388 | 7/1977 | Martini | 260/30.6 |
| 4,094,911 | 6/1978 | Mitsch et al. | 260/615 A |
| 4,118,421 | 10/1978 | Martini | 260/544 F |
| 4,420,434 | 12/1983 | Falk | 260/501.16 |
| 4,729,849 | 3/1988 | Hisamoto et al. | 252/355 |

FOREIGN PATENT DOCUMENTS 1529514 10/1978 United Kingdom ................ 260/535

OTHER PUBLICATIONS

R. E. Banks, Organofluorine Chemicals and Their Applications, Ellis Horwood Ltd., Chichester, 1979, pp. 222-223.
Bernett et al., Surface Properties of Perfluoro Acids as affected by Terminal Branching and Chlorine Substitution, J. Phys. Chem., 71, 1967, p. 2075-2082.
Zisman et al., Properties of Films of Adsorbed fluorinated Acids, J. Phys. Chem., 58, 1954, pp. 236-239.
G. Caporiccio et al., Ind. Eng. Chem. Prod. Res. Dev., Perfluoropolyether Fluids for Vacuum Technologies, 1982, 21, 515-519.
R. E. Banks, Preparation Properties & Industrial Applications of Organofluorine Compounds, Ellis Horwood Ltd., Chichester, 1982, Ch. 1, pp. 19-43.

*Primary Examiner*—Anthony McFarlane
*Attorney, Agent, or Firm*—D. M. Sell; W. N. Kirn; Truesdale C.

[57] ABSTRACT

Perfluoro(cycloaliphatic methyleneoxyalkylene) compositions are provided. These compositions comprise perfluoro(cycloaliphatic methyleneoxyalkylene) carbonyl fluoride compounds having (a) a perfluorocycloaliphatic moiety which can have up to two perfluoroalkyl substituents and a perfluoroalkylene substituent, and (b) a perfluoromethyleneoxyalkylene carbonyl fluoride radical, the methylene group of the radical being bonded to a ring carbon atom or the perfluoroalkylene substituent of the moiety and the alkylene group of the perfluoromethyleneoxyalkylene carbonyl fluoride being a perfluoro(methyl)methylene group, a perfluoroisopropyleneoxy(methyl)methylene group, or a poly(perfluoroisopropyleneoxy)perfluoro(methyl)methylene group having up to about 10 perfluoroisopropyleneoxy units. Also provided are functional derivatives of the perfluoro(cycloaliphatic methyleneoxyalkylene) carbonyl fluoride compounds and nonfunctional derivatives of the perfluoro(cycloaliphatic methyleneoxyalkylene) carbonyl fluoride compounds.

11 Claims, No Drawings

PERFLUORO(CYCLOALIPHATIC METHYLENEOXYALKYLENE) CARBONYL FLUORIDES AND DERIVATIVES THEREOF

This invention relates to perfluoroaliphatic ether-containing carbonyl fluoride compositions and derivatives thereof, and a method of preparing same.

The preparation of perfluoroalkoxypropionic acid fluorides by reaction of hexafluoropropylene oxide,

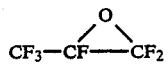

with perfluorocarboxylic acid fluorides is known.

U.S. Pat. No. 3,250,808 (Moore et al.) discloses the reaction of hexafluoropropylene oxide with itself, fluoroalkanoic acid fluorides, or fluoroalkanones to produce fluorocarbon ethers having the formulas $R_fO[CF(CF_3)CF_2O]_n-CF(CF_3)COX$ and $R_fO[CF(CF_3)CF_2O]_nCF(CF_3)COOM$ where $R_f$ is a fluoroalkyl radical or a fluoroalkoxyalkyl radical, n is a number from zero on up, X is an amino radical, a halogen radical or a hydroxyl radical, and M is an alkyl radical, a metallic cation or an ammonium group.

British Pat. No. 1,529,514 (duPont) discloses the reaction of hexafluoropropylene oxide with fluorinated carbonyl compounds of the general formula $R_aR_bC=O$ wherein $R_a$ and $R_b$ each independently represent fluoroine, a fluoroalkyl group of one to fourteen carbon atoms, a sulfonyl-substituted fluoroalkyl group of one to fourteen carbon atoms, a fluoroalkoxy group of one to fourteen carbon atoms, a sulfonyl-substituted fluoroalkoxy group of one to fourteen carbon atoms, a fluoroalkoxyalkyl group of two to fourteen carbon atoms and one to six oxygen atoms or a sulfonyl-substituted fluoroalkoxyalkyl group of two to fourteen carbon atoms and one to six oxygen atoms to provide acid fluoride-containing ethers of the general formula $R_aR_b$-CFOCF(CF_3)COF$.

U.S. Pat. No. 4,035,388 (Martini) discloses a process for preparing perfluoro-α-alkoxypropionic acid fluorides of the general formula $R^1O[CF(CF_3)CF_2O]_nCF(CF_3)COF$ wherein $R^1$ stands for a perfluoroalkyl radical having from 1 to 9 carbon atoms or for the radical $CF_3CFOCF_2CF(CF_3)OCF-$ and n is 0, 1, or 2.

U.S. Pat. No. 4,118,421 (Martini) discloses a process for preparing perfluoroalkoxypropionic acid fluorides of the formula $R_fO[CF(CF_3)CF_2O]_nCF(CF_3)COF$.

U.S. Pat. No. 3,271,341 (Garrison, Jr.) discloses ionizable dispersing agents useful in the preparation of aqueous colloidal polymer dispersions, the dispersing agents being water-soluble compounds having the general formula $F(CF_2)_mO[CF(X)-CF_2-O]_n-CF(X)-COOA$ where X is a member of the class consisting of fluorine and the perfluoromethyl radical, m is a positive integer of 1 to 5 inclusive and n is a positive integer from 0 to 10 and A is a hydrophilic radical of the class consisting of hydrogen and monovalent salt radicals.

Certain patents disclose functional perfluorocycloaliphatic compositions. U.S. Pat. No. 2,593,737 (Diesslin et al.) discloses cyclic fluorocarbon monocarboxylic acids represented by the formulas $C_6F_{11}COOH$ and $C_6F_{11}CF_2COOH$, and their functional derivatives. U.S. Pat. Nos. 3,600,433 (Holland et al.) and 3,699,156 (Holland et al.) disclose cyclic fluorocarbon compounds of the general formula $R_f'C_6F_{10}COF$, $R_f'C_6F_{10}CH_2OH$, and $C_6F_{11}CH_2OH$ and their functional derivatives.

It has long been accepted that among fluorinated surfactants of the same carbon number, straight chain products generally give lower surface tension in aqueous solutions than do branched chain products. R. E. Banks (*Organofluorine Chemicals and Their Applications*, Ellis Horwood Ltd., Chichester, 1979, p. 222-223) discloses that, except at very low concentrations (<0.01%, 100 ppm), the lower surface tension is attained with the straight-chain fluorochemical products than with the branched chain fluorochemical products. Marianne K. Bernett and W. A. Zisman (Surface Properties of Perfluoro Acids as Affected by Terminal Branching and Chlorine Substitution, *J. Phys. Chem.*, 71,1967, p. 2075–2082) show that a condensed monolayer of a fully fluorinated straight chain alkanoic acid has a lower critical surface tension than its terminally branched analogue with the same chain length. In earlier work, E. F. Hare, E. G. Shafrin and D. A. Zisman (Properties of Films of Adsorbed Fluorinated Acids, *J. Phys. Chem.*, 58, 1954, p. 236–239) postulate that the remarkable non-wettability of a condensed monolayer of a fully fluorinated straight chain alkanoic acid and its resulting low critical surface tension is due to formation of a surface of closely packed $-CF_3$ groups.

It has now surprisingly been found that certain highly branched fluorochemical products can provide an aqueous solution with low surface tension, particularly at high concentrations, e.g., 500 to 10,000 ppm as well as at low concentrations, e.g., 50–100 ppm.

This invention provides perfluoro(cycloaliphatic methyleneoxyalkylene) compositions comprising (1) perfluoro(cycloaliphatic methyleneoxyalkylene) carbonyl fluoride compounds having (a) a perfluorocycloaliphatic moiety which can have up to two perfluoroalkyl substituents and a perfluoroalkylene substituent, and (b) a perfluoromethyleneoxyalkylene carbonyl fluoride radical, the methylene group of the radical being bonded to a ring carbon atom or the perfluoroalkylene substituent of the perfluorocycloaliphatic moiety and the alkylene group of the perfluoromethyleneoxyalkylene carbonyl fluoride being a perfluoro(methyl)methylene group, a perfluoroisopropyleneoxy(methyl)methylene group, or a poly(perfluoroisopropyleneoxy)perfluoro(methyl)methylene group having up to about 10 perfluoroisopropyleneoxy units, (2) functional derivatives of the perfluoro(cycloaliphatic methyleneoxyalkylene) carbonyl fluoride compounds, or (3) nonfunctional derivatives of the perfluoro(cycloaliphatic methyleneoxyalkylene) carbonyl fluoride compounds. The functional and nonfunctional derivatives have the perfluorocycloaliphatic moiety and the perfluoromethyleneoxyalkylene group of the perfluoromethyleneoxyalkylene carbonyl fluoride intact.

The perfluorocycloaliphatic moiety is preferably a perfluorocyclohexyl or a perfluorodecalin moiety which may contain as ring atoms, an oxygen or nitrogen hetero atom or both, the perfluoroalkyl substituents, when present on the perfluorocycloaliphatic moiety, are straight or branched chain and preferably have 1 to 4 carbon atoms, and the perfluoroalkylene substituent, when present on the perfluorocycloaliphatic moiety, preferably has 1 to 6 carbon atoms. The functional derivatives of the carbonyl fluoride compounds include, for example, carboxylic acids and their salts, esters, amides, nitriles, alcohols, acrylates, and vinyl ethers. The nonfunctional derivatives of the carbonyl fluoride compounds include for example, hydrides, fluorides, and chlorides.

The derivatives of the perfluoro(cycloaliphatic methyleneoxyalkylene) carbonyl fluorides of the present invention have utility for various applications, such as surfactants, elastomers, coatings, lubricants, heat transfer and cooling fluids, hydraulic fluids, vapor phase heating, and in the treatment of fibrous substrates to impart oil and water repellency thereto. The ammonium salts of the carboxylic acid derivatives of the present invention are particularly useful as surfactants, i.e., for lowering the surface tension of aqueous solutions.

These perfluoro(cycloaliphatic methyleneoxyalkylene) compounds can be represented by the formula $$R_f CF_2 O[CFCF_2 O]_n CFZ \quad \quad I$$
$$\quad \quad \quad | \quad \quad \quad \quad \quad |$$
$$\quad \quad \quad CF_3 \quad \quad \quad \quad CF_3$$

wherein $R_f$ is perfluorocycloaliphatic radical

[structures shown]

wherein each $R_f'$ is independently fluorine or a $C_1$ to $C_4$ straight or branched chain perfluoroalkyl radical with the proviso that no more than two $R_f'$ radicals in an $R_f$ radical are said perfluoroalkyl radicals and a is an integer of from 1 to 6, n is 0 to about 10, preferably 0, 1, or 2, Z is —COF or a functional or nonfunctional derivative thereof where Z is —H, —X, —CF$_2$H, —CF$_2$X, —CH$_2$OH, —COX, —COR, —COOH, —COOM$_{1/v}$, —COOR, —CF$_3$, —CONR'R', —CH$_2$NH$_2$, —CH$_2$NCO, —CN, —CH$_2$OCOR$_f$, —CH$_2$OSO$_2$R$_f$, —C$_3$N$_3$(R$_f''$)$_2$, —CH$_2$OCOR, —CH$_2$OCOCR''=CH$_2$, or (CH$_2$)$_m$Si(R''')$_3$, wherein —X is —F, —Cl, —Br, or —I, M is an ammonium radical or a metal atom, v is the valence of M and is 1, 2, or 3, R and R' are each independently H or lower alkyl, e.g., with 1–18 carbom atoms, aryl, e.g., with 6, 10, or 12 ring carbon atoms, or a combination thereof, i.e., alkylaryl or arylalkyl or the two R' groups in —CONR'R' can together form an alkylene moiety, e.g., with 2 to 6 carbon atoms, which together with the amido nitrogen atom form a heterocyclic ring, e.g., —NC$_5$H$_{10}$ or C$_2$H$_4$OC$_2$H$_4$N—, R'' is —H or —CH$_3$, R''' is a hydrolyzable group such as methoxy, R$_f''$ is a fluoroaliphatic group, e.g., perfluoroalkyl, which can contain one or a plurality, e.g., 2 to 4, of hetero atoms, such as catenary oxygen or nitrogen atoms, e.g., perfluoroalkoxyalkyl, said fluoroaliphatic groups having, e.g., 1 to 21 carbon atoms, preferably 1 to 4 catenary carbon atoms, particularly where R$_f''$ is perfluoroalkyl, and m is an integer of 2 to 11.

In the structural formulas, above and elsewhere, the "F" within a ring structure conventionally denotes that the ring is perfluoro, i.e., all the ring carbon atoms are bonded to fluorine atoms and also may be bonded to substituents, e.g., CF$_3$ or C$_4$F$_9$.

As can be seen from the above formula, the compounds of the invention, in general, are highly branched. Lateral branching occurs at the pendant methyl groups of the perfluoro(methyl)methylene and the perfluoroisopropyleneoxy unit. Forked branching occurs at the juncture of the perfluorocycloaliphatic moiety with either the perfluoromethylene group or the perfluoroalkylene substituent as well as with the perfluoroalkyl substituents.

The perfluoro(cycloaliphatic methyleneoxyalkylene) carbonyl fluorides of this invention can be prepared by the catalyzed reaction of hexafluoropropylene oxide with perfluorocycloaliphatic carbonyl fluoride precursor compounds.

The perfluorocycloaliphatic carbonyl fluoride precursor compounds are selected from perfluorocyclohexane carbonyl fluoride, perfluorodecalin carbonyl fluoride, 1-azaperfluorocyclohexane-1-alkane carbonyl fluoride, 1-oxa-4-azacyclohexane-4-alkane carbonyl fluoride, and ring-carbon C$_1$ to C$_4$ perfluoroalkyl mono- and di-substituted analogs of these compounds.

These precursor carbonyl fluoride compounds are conveniently prepared from hydrocarbon precursors by electrochemical fluorination (ECF), for example,

[reaction scheme: benzene-COCl + HF →ECF→ perfluorocyclohexane-COF]

Electrochemical fluorination is described, for example, in U.S. Pat. No. 2,593,737 (Diesslin et al.) which is incorporated by reference herein for that purpose. In electrochemical fluorination involving 6-membered ring hydrocarbon precursors, a minor amount of ring opening and ring contraction typically takes place resulting in trifluoromethyl-substituted 5-member ring by-product. For example, in the above reaction, up to about 20 weight percent of perfluoro(methylcyclopentane) carbonyl fluoride is formed. This by-product is difficult to separate by distillation as it has the same boiling point as the principal 6-member ring product. The presence of the 5-member ring by-product is not detrimental to compositions of the present invention. The 5-member ring by-product reacts with the hexafluoropropylene oxide, as does the 6-member ring product, and yields useful adducts and derivatives of the adducts. Thus, most of the compositions of this invention will contain such ring-contracted by-products. (Ring contraction in electrochemical fluorination is described, for example, in *Preparation, Properties and Industrial Applications of Organofluorine Compounds*, R. E. Banks, Ed., Ellis Horwook Ltd., Chichester, 1982, Ch. 1, p. 19–43.)

The catalyzed reaction of the perfluorocycloaliphatic carbonyl fluoride precursors with hexafluoropropylene oxide can be schematically described by the following equation:

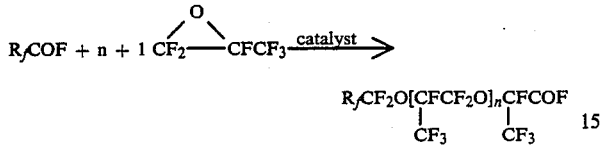

In this reaction, the carbonyl fluoride, —COF, of the precursor carbonyl fluoride compound is converted to a perfluoromethyleneoxy group, —$CF_2O$—, of the perfluorocycloaliphatic methyleneoxyalkylene) carbonyl fluoride product.

Various catalytic processes for use with hexafluoropropylene oxide are well known to those skilled in the art. The preferred catalytic process for the reaction of hexafluoropropylene oxide with a perfluorocycloaliphatic carbonyl fluoride is carried out in a polar organic solvent, such as glyme, in the presence of alkali metal iodides or bromides, preferably potassium iodide or potassium bromide. Reaction temperatures can vary widely, e.g., from about −80° to 100° C., preferably −30° to 60° C. The reaction time is generally from several minutes to about 50 hours depending on the scale of the reaction, with larger scale reactions requiring longer times. The reaction is generally carried out at atmospheric pressure, although higher pressure can be used, and requires no special equipment.

To perform the reaction, the solvent and the perfluorocycloaliphatic carbonyl fluoride precursor are charged to the reaction vessel and the catalyst is then added followed by addition of the hexafluoropropylene oxide, or the solvent and catalyst are charged to the reaction vessel and the carbonyl fluoride is added followed by the hexafluoropropylene oxide.

The concentration of the catalyst used is, functionally stated, a catalytic amount, which can be empirically determined. Generally that amount need not exceed about 12 mole percent based on the carbonyl fluoride when potassium iodide is the catalyst. With potassium bromide, it is occasionally necessary to use somewhat larger amounts of catalyst ranging up to 100 mole percent based on the carbonyl fluoride.

Representative perfluoro(cycloaliphatic methyleneoxyalkylene) carbonyl fluoride compositions of this invention include the following:

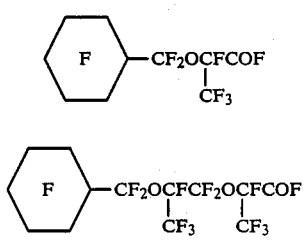

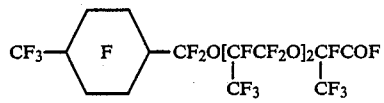

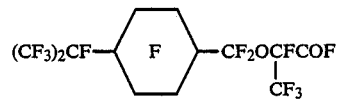

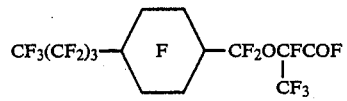

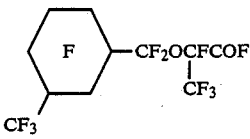

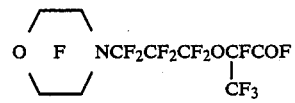

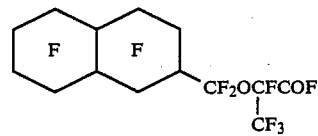

The perfluoro(cycloaliphatic methyleneoxyperfluoroalkylene) carbonyl fluorides of this invention are useful intermediates for the preparation of many derivatives. These derivatives include nonfunctional or functional derivatives such as, for example, carboxylic acids and their salts, esters, amides, nitriles, alcohols, acrylates, and vinyl ethers.

Various patents disclose a host of functional derivatives of oxyperfluoroalkylenes, i.e., perfluoropolyethers, e.g., see U.S. Pat. Nos. 3,250,808 (Moore et al.) and 4,094,911 (Mitsch et al.) which are incorporated herein by reference for this purpose. Perfluoropolyethers with nonfunctional terminal moieties are sold under the trademarks "KRYTOX" and "FOMBLIN" for use as vacuum pump fluids, e.g., see G. Caporiccio et al., Perfluoropolyether Fluids for Vacuum Technologies, *Ind. Eng. Chem. Prod. Res. Dev.*, 1982, 21, 515–519 which is incorporated herein by reference for this purpose.

These derivatives have utility for various applications, such as surfactants, elastomers, coatings, lubricants, heat transfer and cooling fluids, hydraulic fluids, vapor phase heating, and in the treatment of fibrous substrates to impart oil and water repellency thereto. The ammonium salts of the carboxylic acid derivatives are particularly useful as surfactants. For example, the preparation of the ammonium salt is carried out by hydrolyzing the carbonyl fluoride to form an acid, then neutralizing the acid with ammonia. The following equations show these reactions for compound III.

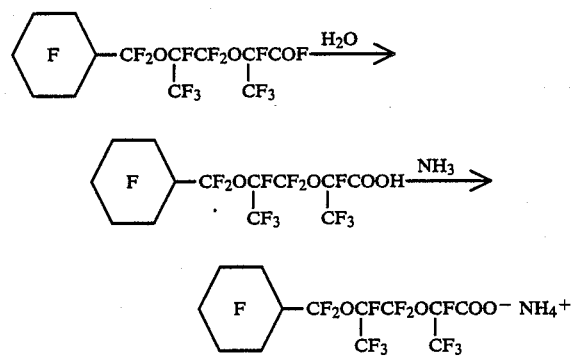

To further illustrate this invention, the following nonlimiting examples are provided. In these examples, amounts are in weight percent unless otherwise indicated.

In the examples, all products had physical and analytical properties which were fully consistent with the composition. Gas chromatographic (GC) analysis of the reaction products, was carried out either on the acid fluoride, using a 3 m 20% SE-52 column, or after conversion of the acid fluoride to the methyl esters, using a 3-meter OV101 column, to give baseline separation of the starting materials and the perfluoro(cycloaliphatic methyleneoxyalkylene) products. Infrared (IR) spectral analysis of the products showed the characteristic carbonyl fluoride stretch at 5.22 microns. Fluorine nuclear magnetic resonance ($^{19}$F NMR) analysis was occasionally complicated by the presence of isomers and non-carbonyl-containing impurities present in the original starting acid fluorides, as well as some overlap in the 75-85 ppm range, but showed the characteristic —COF fluorine at +26 ppm downfield from the internal CFCl$_3$ standard. Gas chromatographic-mass spectral (GC-MS) analysis was also carried out in some cases. Yields were based on GC area percentages corrected for non-hexafluoropropylene oxide derived materials.

EXAMPLE 1

Potassium iodide (5.0 g, 0.03 mole, Fisher, certified ACS) which had been vacuum dried, was added to 50 g dry (by distillation from sodium benzophenone ketyl) diglyme, (CH$_3$OC$_2$H$_4$)$_2$O, (Aldrich Chemical Co., 99%) contained in a 250 ml, 3-necked round bottom flask equipped with a Dry Ice TM -acetone condenser, an overhead stirrer, and a gas inlet. To this stirred mixture was added, all at one, perfluorocyclohexane carbonyl fluoride, C$_6$F$_{11}$COF, (100 g of 85% purity, 0.26 mole). After stirring for one hour at 0° C., hexafluoropropylene oxide (56 g of 80% purity, 0.27 mole) was added through the gas inlet over a period of 45 minutes. After stirring for two hours, the resulting lower fluorochemical phase (143 g) was separated. Analysis of the fluorochemical phase by GC, IR, and $^{19}$F NMR showed that the phase contained 76% perfluoroaliphatic ether-containing carbonyl fluoride products,

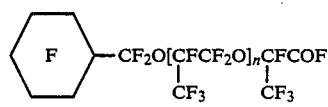

and isomers thereof, with the product distribution being n=0:45%, n=1:38%, and n≧2:17%, for a yield of 57% based on perfluorocyclohexane carbonyl fluoride; 20% unreacted starting acid fluoride; and 4% hexafluoropropylene oxide oligomer, C$_3$F$_7$O[CF(CF$_3$)CF$_2$O]$_p$CF(CF$_3$)COF, where p was 0 to 2.

EXAMPLE 2

Potassium iodide (7.06 g, 0.042 mole) was added to dry diglyme (81 g), which had been distilled from sodium/benzophenone ketyl, contained in a 250 ml, 3-necked round bottom flask equipped with a Dry Ice TM -acetone condenser, an overhead stirrer, and a gas inlet. To this stirred mixture was added perfluoro(4-methylcyclohexane carbonyl fluoride) (163.5 g of 82% purity, 0.355 mole) and the mixture was cooled to 0° C. over a twenty minute period. Hexafluoropropylene oxide (65.4 g, 0.394 mole) was added over one hour and the reaction mixture was stirred for two hours and then allowed to warm to room temperature. The resulting lower fluorochemical phase (207 g) was separated. Analysis of the fluorochemical phase by GC and IR, as well as GC-MS of the methyl ester, showed that the phase contained 59% perfluoro(cycloaliphatic methyleneoxyalkylene) carbonyl fluoride compounds,

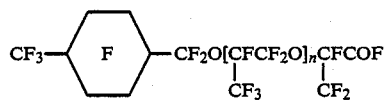

and isomers thereof, with the product distribution being n=0:51%, n=1:41%, and n=2:8%, in yield of 55% based on the starting carbonyl fluoride.

EXAMPLE 3

The product of Example 2 was distilled and the cut boiling at 60°-68° C./30 torr was collected. GC analysis of the methyl ester showed that this fraction contained 95% product where m=0. This fraction (10 g) was hydrolyzed by stirring with 20 ml water for two hours, followed by separation of the resulting lower fluorochemical phase which was taken up in Freon TM 113, washed twice with water, dried over magnesium sulfate, and distilled yield 7.84 g of a clear, viscous acid (boiling point: 82°-84° C./0.1 torr),

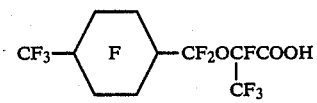

and isomers thereof. The IR spectrum of the product showed a broad —OH stretch at 3.2 microns and a very strong carbonyl stretch at 5.65 microns consistent with the acid product.

EXAMPLE 4

A portion (7.7 g) of the acid product of Example 3 was dissolved in 60 ml of Freon TM 113 in a 100 ml 3-necked, round bottom flask equipped with a condenser and a gas inlet tube reaching below the surface of the solution. Anhydrous ammonia was passed through the solution until IR analysis showed that the carbonyl stretch of 5.65 microns for starting acid was no longer present and a band at 6.0 microns for the ammonium salt was present. The solvent was evaporated and the resulting white solid,

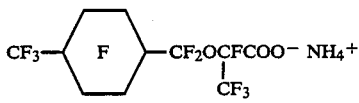

and isomers thereof, was isolated. This ammonium salt did not melt, but decomposed when heated at 205°–210° C. with evolution of ammonia.

EXAMPLE 5

A perfluoro(cycloaliphatic methyleneoxyalkylene) carbonyl fluoride,

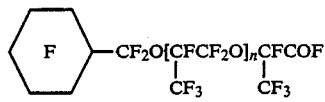

and isomers thereof, with the product distribution being n=0:94% and n=1:6% as determined by GC analysis of the methyl ester, was prepared as in Example 1. This product (15 g, 0.03 mole) was added to 50 g of a solution of 30% $BF_3$ in methanol and stirred at room temperature for one hour. The resulting lower fluorochemical phase was separated and washed twice with saturated aqueous sodium chloride solution to yield 13.6 g (89%) of methyl esters,

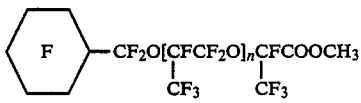

and isomers thereof, with the product distribution being n=0:95% and n=1:5%. IR analysis showed a sharp, weak band at 3.3 microns for the —$CH_3$ stretch and a strong carbonyl stretch at 5.52 microns. The structures were further confirmed by GC-MS which showed parent ions for the expected methyl esters.

EXAMPLE 6

The ester of Example 5 (11.5 g) was dissolved in 70 ml methanol containing 5 ml Freon TM 113. Anhydrous ammonia was passed through the solution until the solution became slightly basic. The resulting solution was stirred at room temperature (about 22° C.) overnight. To complete reaction of the ester with ammonia, the solution was heated to reflux while passing ammonia through the mixture. The ester rapidly reacted under reflux conditions. The reaction mixture ws poured into water and taken up with additional Freon TM 113, washed with water and the resulting lower fluorochemical phase separated and dried over sodium sulfate and the solvent was removed, yielding 9.2 g of a white, waxy solid (melting point: 55°–59° C.),

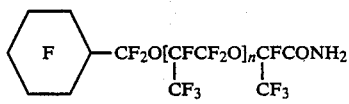

and isomers thereof, with a product distribution of n=0:95% and n=1:5%. IR analysis showed a doublet at 2.86 and 3.1 microns for the —$NH_2$ stretch as well as the carbonyl stretch at 5.82 microns. GC-MS confirmed the amide structure, showing the expected parent ions.

EXAMPLE 7

The amide of Example 6 (9.2 g) was placed in a 100 ml round bottom flask and phosphorous pentoxide (20 g) was added and the mixture was stirred until homogeneous. A short path distillation head was attached to the flask and the flask was placed in an oil bath. The oil bath was slowly heated to 195° C. and held at that temperature for 150 minutes. During this time a small amount of liquid distilled and reflux of liquid in the flask was noted. At the end of this time, the distillation head was attached to a water aspirator and vacuum was applied to flash distill the liquid remaining in the flask and yield 8.4 g of a clear liquid nitrile,

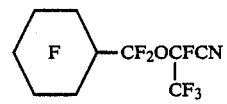

and isomer thereof. IR analysis showed the absence of starting amide bands above 3.0 microns and the carbonyl band at 5.82 microns and the presence of the nitrile stretch at 4.37 microns as a shrp, weak band. GC-MS confirmed the nitrile structure and showed the corresponding parent ions of the various oligomeric and ring-contracted products.

EXAMPLE 8

Potassium iodide (3.56 g, 0.021 mole) was added to dry diglyme (94 g) contained in a 250 ml, 3-necked, round bottom flask equipped with a Dry Ice TM -acetone condenser, an overhead stirrer and a gas inlet. To this stirred mixture was added perfluoro(4-isopropylcyclohexane)carbonyl fluoride (147 g of 58% purity, 0.179 mole). The reaction mixture was cooled to 0° C. over a period of about 25 minutes. Hexafluoropropylene oxide (32.7 g, 0.197 mole) was slowly added over a 30 minute period. The resulting mixture was stirred for four hours and then allowed to warm to room temperature. The resulting lower fluorochemical phase (166 g) was separated yielding perfluoro(cycloaliphatic methyleneoxyalkylene) carbonyl fluoride compounds (26%),

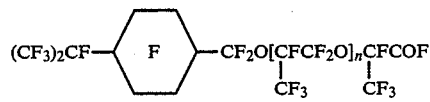

and isomers thereof, with the product distribution being n=0:81% and n=1:19%, as determined by GC analysis of the methyl ester, and the yield being 35% based on the starting carbonyl fluoride. The structures were further confirmed by GC-MS which showed parent ions for the expected methyl esters.

EXAMPLE 9

The product of Example 8 was distilled and the fraction boiling at 68°–86° C./15 torr was collected. A portion of this fraction (15 g) having a distribution of n=0:93% and n=1:7%, was added to 30 ml of water and hydrolyzed as in Example 3. This hydrolyzed product was distilled to yield the acid product (6.7 g, boiling point: 87° C./0.5 torr),

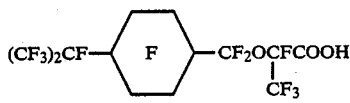

and isomers thereof. IR analysis showed the broad —OH stretch centered at 3.1 microns and the acid carbonyl at 5.64 microns.

EXAMPLE 10

The acid product of Example 9 (6.2 g) was dissolved in 50 ml Freon ™ 113 and anhydrous ammonia was passed through the resulting solution until the solution was just basic to pH paper. The solvent was evaporated to yield a pale yellow solid product (5.54 g),

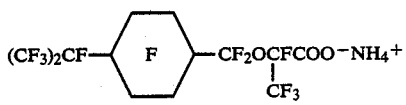

and isomers thereof. IR analysis showed the carbonyl band at 6.0 microns as well as a strong and broad band for the ammonium ion at 3.2 microns. The melting point was 187°–202° C. with decomposition and evolution of ammonia.

EXAMPLE 11

Using the procedure of Example 1, potassium bromide (2.59 g, 0.022 mole) diglyme (100 g), and perfluoro(morpholinopropionyl) fluoride (100 g of 68% purity, 0.18 mole) were combined and stirred at 25% for one hour. The reaction mixture was cooled to 0° C. and hexafluoropropylene oxide (40 g of 80% purity, 0.19 mole) was added over a period of 30 minutes. After an additional period of about 4 hours of stirring, the reaction mixture was allowed to warm to about 25° C. over a 2-hour period. The resulting lower fluorochemical phase yielded (52%) perfluoro(cycloaliphatic methyleneoxyalkylene) carbonyl fluoride compounds,

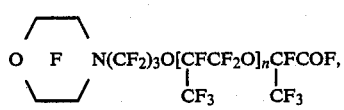

with the product distribution being n=0:79%, n=1:12%, and n=2:9%, as determined by GC of the methyl esters, and the yield being 60% based on the starting carbonyl fluoride.

This product was distilled and hydrolyzed as in Example 3 and then reacted with anhydrous ammonia and dried as in Example 4 to yield a solid product,

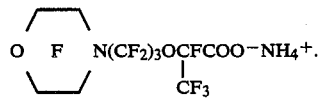

The melting point of this product was 164°–175° C. with decomposition and evolution of ammonia. GC-MS of the corresponding methyl ester prepared by reaction of the acid fluoride with diazomethane further confirmed the structure.

EXAMPLE 12

A perfluoro(cycloaliphatic methyleneoxyalkylene) carbonyl fluoride was prepared using a procedure similar to that in Example 1 to yield

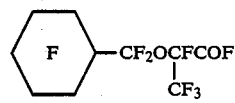

and isomers thereof. This product was distilled through a 3-plate Snyder column with a reflux splitter. The fraction was distilled at 124°–160° C. at atmospheric pressure to yield, as determined by GC of the methyl esters,

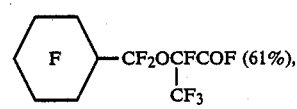

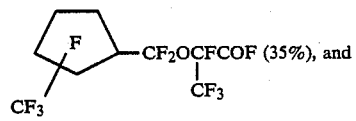

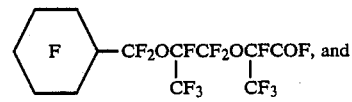

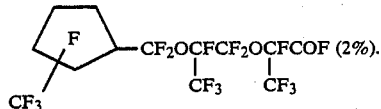

This fraction (538 g) was hydrolyzed by stirring with 500 ml of water. After 30 minutes, the resulting fluorochemical phase was separated and washed with 100 g of 96% concentrated sulfuric acid. This phase was then distilled at 0.05 torr at a head temperature of 78°–86° C. to give 456 g of a clear liquid acid product,

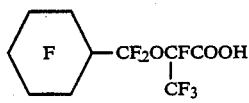

and isomers thereof. IR and GC-MS confirmed the product identity.

EXAMPLE 13

The product of Example 12 (444 g) was dissolved in 600 g of Freon ™ and placed in a flask fitted with a gas inlet tube and a −78° C. condenser. A total of 26 g of gaseous ammonia was added before the solution tested basic on wet pH paper, at which time the reaction mixture was very viscous. The flask contents were poured into a glass tray, dried overnight at room temperature, then dried at 70° C. for another eight hours. Ammonium salt (400 g, white solid),

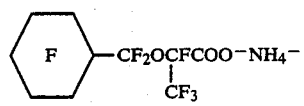

and its perfluoromethylcyclopentyl isomers, was isolated. $^{19}$F NMR and IR analysis were consistent for this product.

EXAMPLE 14

Acid product (20 g) prepared using a procedure similar to that in Example 12 was added to a round bottom flask. Lithium hydroxide (1.1 g) was dissolved in 80 ml of water. This solution of lithium hydroxide was added to the flask until the solution tested basic. The reaction mixture was poured into a crystallizing dish and dried at 90° C. overnight. Lithium salt (19.4 g, white solid),

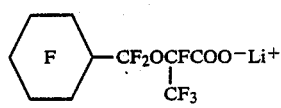

and isomers thereof, was isolated. IR analysis was consistent for this product.

EXAMPLE 15

Acid product (20 g) prepared using a procedure similar to that in Example 12 was added to a round bottom flask. Potassium hydroxide (2.8 g) was dissolved in 80 ml of water. This solution of potassium hydroxide was added to the flask until the solution tested basic. The reaction mixture was poured into a crystallizing dish and dried at 93° C. overnight. Potassium salt (20.9 g, white solid),

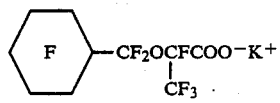

and isomers thereof, was isolated. IR analysis was consistent for this product.

EXAMPLE 16

Acid product (10 g), prepared using a procedure similar to that in Example 12, was added to a round bottom flask. Barium hydroxide (3.5 g) was dissolved in 80 ml of water. This solution of barium hydroxide was added to the flask until the solution tested basic. The reaction mixture was poured into a crystallizing dish and dried at 93° C. overnight. Barium salt (11.3 g, white solid),

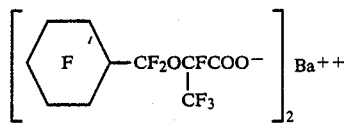

and isomers thereof, was isolated. IR analysis was consistent for this product.

EXAMPLE 17

Acid product (10 g), prepared using a procedure similar to that in Example 12, was added to a round bottom flask. Dimethylamine (40% aqueous, 3.0 g) was added to the flask until the solution tested basic. The reaction mixture was poured into a crystallizing dish and dried at 75° C. overnight. Amine salt (10.8 g, white solid),

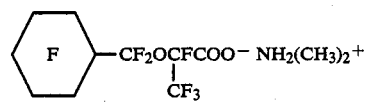

and isomers thereof, was isolated. IR analysis was consistent for this product.

EXAMPLE 18

A perfluoro(cycloaliphatic methyleneoxyalkylene) carbonyl fluoride,

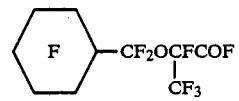

and isomers thereof, was prepared using a procedure similar to that of Example 1. This product was distilled through a 3-plate Snyder column with a reflux splitter. The major product fraction distilled at 75°-89° C. at 100 torr. GC analysis of the acid fluoride showed this material to be

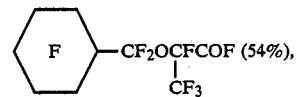

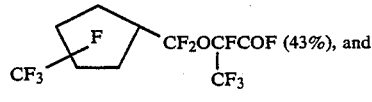

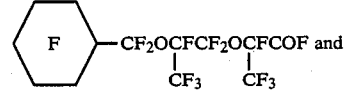

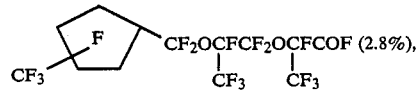

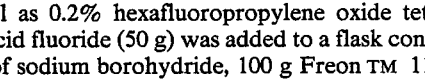

as well as 0.2% hexafluoropropylene oxide tetramer. This acid fluoride (50 g) was added to a flask containing 3.8 g of sodium borohydride, 100 g Freon ™ 113, and 10 g tetraglyme over a period of 1.5 hours. The reaction mixture was heated for 3 hours at 40°-50° C., then cooled to room temperature and poured into 50 ml of water. The resulting reaction mixture was acidified to pH 3 by the addition of 5 g of concentrated sulfuric acid and the resulting lower fluorochemical phase was drained off. This lower fluorochemical phase was washed with 50 ml of water which had 1 g sodium chloride dissolved therein. The fluorochemical phase was stripped at atmospheric pressure until the flask temperature was 105° C. The resulting residue was distilled at 45 torr through a 3-plate Snyder column with a reflux splitter. The resulting clear liquid alcohol (32 g),

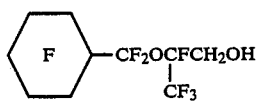

and isomers thereof, distilled at a temperature of 92°-110° C. at 45 torr. $^{19}$F NMR and IR were consistent for this product.

EXAMPLE 19

A perfluoro(cycloaliphatic methyleneoxyalkylene) carbonyl fluoride,

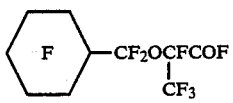

and isomers thereof, was prepared using a procedure similar to that of Example 1 and was distilled until the distillation head temperature reached 160° C. and the temperature of the residue in the distillation flask reached 180° C. Analysis of the residue in the distillation flask by GC as the acid fluoride showed this material to be

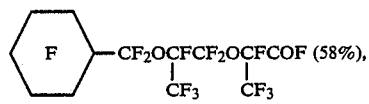

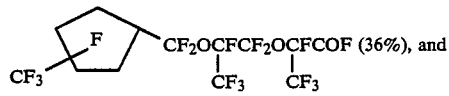

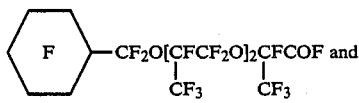

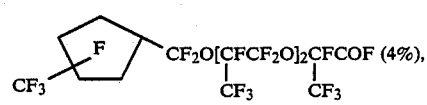

as well as 2% hexafluoropropylene oxide tetramer. This distillation flask residue was hydrolyzed to its corresponding acid by adding 124 ml water to the residue (183 g) with stirring to effect hydrolysis. After 30 minutes, the resulting lower fluorochemical layer was separated and distilled at 0.3 torr at a head temperature of 105°-120° C. to yield a clear, thick liquid acid product,

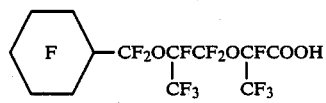

and its isomers. IR analysis consistent for this product.

EXAMPLE 20

The acid product of Example 19 (96 g) was dissolved in 200 g Freon TM 113 and placed in a flask fitted with a gas inlet tube and a −78° C. condenser. Gaseous ammonia (3 g) was added to the flask until the solution tested basic on wet pH paper at which time the reaction mixture was very viscous. The flask contents were poured into a glass tray, dried overnight at room temperature, then dried at 70° C. for eight hours. A white solid ammonium salt (88 g),

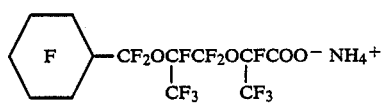

and its perfluoromethylcyclopentyl isomers, was isolated. $^{19}$F NMR and IR were consistent with this product.

EXAMPLE 21

Hexafluoropropylene oxide was reacted with perfluorocyclohexane carbonyl fluoride at a molar ratio of 2:1. This product was fractionally distilled through a 3-plate Snyder column with a reflux splitter. The major product fraction distilled at 93°-114° C. at 40 torr. GC analysis of the acid fluoride showed this material to be

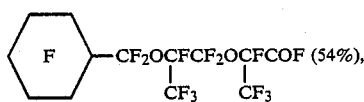

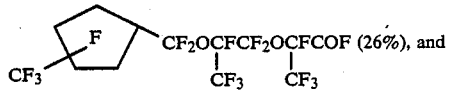

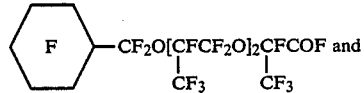

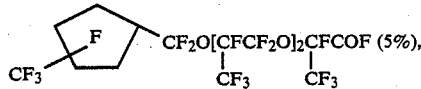

as well as 4% hexafluoropropylene oxide tetramer. This fraction was converted to its dihydroalcohol by adding the fraction to a flask containing 6.3 g sodium borohydride and 100 g of acetonitrile over a period of 30 minutes. The reaction mixture was heated for 3 hours at 70°-80° C., then cooled to room temperature, and poured into 100 ml of water. The reaction mixture was acidified to pH 3 by the addition of 8 g concentrated sulfuric acid and the resulting lower fluorochemical phase was drained off. This phase was washed with 50 ml of water which had 1 g sodium chloride dissolved therein and stripped at atmospheric pressure until the pot temperature reached 96° C. The resulting residue was distilled at 1.0 torr through a 3-plate Snyder column with a reflux splitter. A slightly yellow liquid alcohol product (74 g),

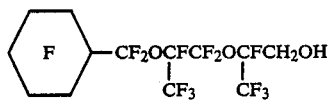

and isomers thereof, distilled at a head temperature of 82°-102° C. at 1.0 torr. IR and GC-MS analysis were consistent with this product.

EXAMPLE 22

Potassium iodide (2.4 g, 0.014 mole) and tetraglyme (40 g, 100-190 ppm water) were combined as described in Example 2. Perfluorodecalin carbonyl fluoride (109 g of 54% purity, 0.12 mole) was added and the mixture was stirred at room temperature for 30 minutes. The mixture was cooled to 0° C. over a 5 minute period. Hexafluoropropylene oxide (25 g, 0.15 mole) was added over 1 hour, the reaction mixture was allowed to stir for 45 minutes, and then allowed to warm to room temperature with stirring overnight. The resulting lower fluorochemical phase (127 g) was separated. Analysis by GC of the methyl ester showed the reaction product to contain lower boiling inert material (53%), unreacted perfluorodecalin carbonyl fluoride (28%),

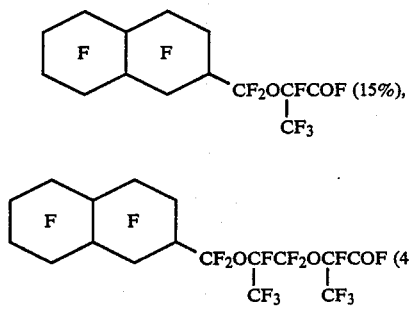

and isomers thereof, a yield of 29% based on the starting acid fluoride. Identity of the product was confirmed by GC-MS of the methyl esters.

EXAMPLE 23

The product of Example 22 was distilled and the fraction boiling at a head temperature of 52°-67° C at 1.0 torr was collected. GC analysis showed that this product contained

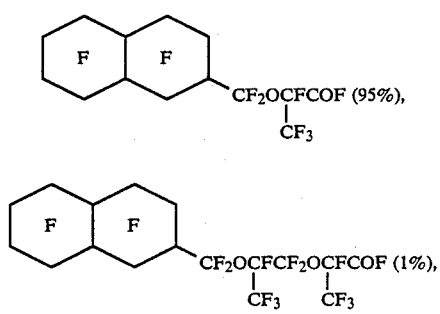

and isomers thereof. This fraction (9.6 g) was placed in a polyethylene bottle with 10 ml of water and shaken for 5 minutes to effect hydrolysis. The resulting lower fluorochemical phase was drained and distilled at 0.1 torr. A clear liquid acid product (6.7 g),

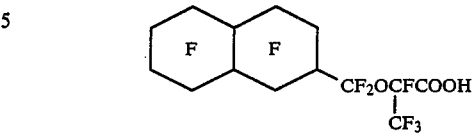

and isomers thereof, distilled at 99°-109° C. at 0.1 torr. IR analysis was consistent with this product and its isomers. Derivatization of this product with diazomethane afforded the methyl ester and subsequent GC-MS showed the major peak to have a molecular weight of 668.

EXAMPLE 24

A portion of the acid product (5.6 g) of Example 23 was poured into a crystallizing dish. Ammonium hydroxide (30% NH3, 3.2 g) was dripped onto the acid, a watch glass was placed on top of the dish, and the dish was rotated 90° back and forth for 5 minutes. The reaction mixture was allowed to stand for 15 minutes and the pH of the reaction mixture was found to be basic. The reaction mixture was stirred vigorously with a spatula and dried overnight at 70° C. The resulting yellow solid ammonium salt (5.5 g),

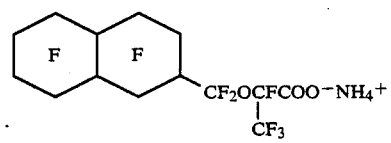

and isomers thereof, was isolated. IR analysis was consistent with this product.

EXAMPLE 25

Hexafluoropropylene oxide was reacted with perfluorocyclohexane carbonyl fluoride at a molar ratio of 2:1. The resulting acid fluoride product was fractionally distilled at 22-56 torr. The major product fraction (2:1 adduct) distilled at 57°-63° C. at 30-35 torr. The product fraction of interest (3:1 adduct) distilled at 64°-82° C. at 22-25 torr. GC analysis showed the product distribution of this fraction to be

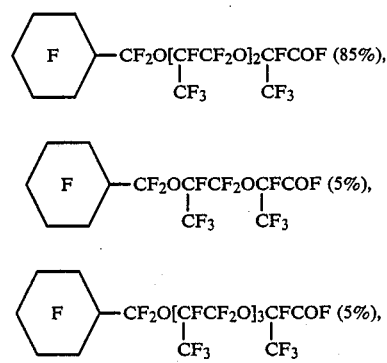

and the perfluoromethylcyclopentyl isomers thereof. To this carbonyl fluoride fraction (53.6 g) was added, with stirring, 50 ml of water to effect hydrolysis. After 30 minutes, 50 g of Freon TM 113 was added and the resulting lower fluorochemical phase was removed. This fluorochemical phase was stripped on a rotary evaporator until the Freon TM was removed and the residue was then distilled at 0.1 torr vacuum. The resulting clear, thick liquid, acid product (40.7 g),

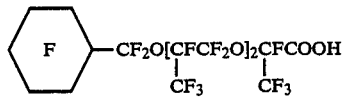

and isomers thereof, distilled at a head temperature of 100°-104° C. at 0.1 torr. GC-MS of the distilled material after derivatization with diazomethane was consistent for this acid product.

EXAMPLE 26

A portion of the acid product (39.0 g) of Example 25 was dissolved in 100 g Freon TM 113 and ammonium hydroxide (30% $NH_3$, 3.0 g) was added dropwise to give a solution pH of 6. The reaction mixture was poured into a crystallizing dish and dried at 60° C. overnight. A white, waxy solid ammonium salt (40 g),

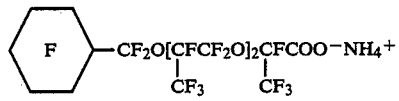

and isomers thereof, was isolated. $^{19}F$ NMR analysis was consistent with this product.

EXAMPLE 27

A portion of the alcohol (50 g) of Example 21 ws dissolved in 100 g Freon TM 113 and placed in a round bottom flask fitted with an overhead stirrer, thermometer, addition funnel, and reflux condenser. Triethylamine (9.5 g ) and a small quantity (5 mg) of the monomethyl ether of hydroquinone were added to the reaction flask. Acryloyl chloride (8.5 g) was added slowly with stirring, maintaining the reaction temperature below 40° C. The reaction mixture was stirred for 30 minutes after the addition of the acryloyl chloride was completed. Potassium hydroxide (200 ml of 3% aqueous) was added and the resulting lower phase of the reaction mixture was separated, washed with hydrochloric acid (100 ml of 5% aqueous), and then washed with distilled water (100 ml). The Freon TM 113 was removed at aspirator pressure on the rotary evaporator, and the residue distilled at 89°-98° C. and 0.3 torr to yield clear liquid acrylate ester (38.7 g),

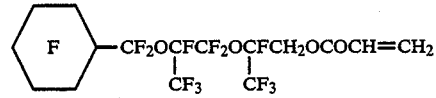

and perfluoromethylcyclopentyl isomers thereof. IR and GC-MS analysis were consistent with this product.

EXAMPLES 28-35 AND COMPARATIVE EXAMPLES C1-C5

In Examples 28-35, the perfluoro(cycloaliphatic methyleneoxyperfluoroalkylene) carboxylate ammonium salts of this invention which were prepared according to the procedures of Examples 4, 10, 11, 13, 24, and 26 were evaluated as surfactants by determining the aqueous surface tensions at various concentrations using a du Nouy interfacial tensiometer. In Comparative Examples C1-C5, perfluoroalkanoic and perfluoro-α-alkoxypropionic carboxylate ammonium salts were similarly tested as surfactants. The results are set forth in Table I with the "Product tested" being the primary, desired reaction product although isomers thereof were also present as previously described.

TABLE I

| | | Surface tension (dynes/cm) | | | | | |
|---|---|---|---|---|---|---|---|
| Example | Product tested | 50 ppm | 100 ppm | 500 ppm | 1000 ppm | 5000 ppm | 10,000 ppm |
| C1 | $CF_3(CF_2)_3OCF(CF_3)COO^- NH_4^+$ | 66.4 | 63.7 | 55.6 | 49.8 | 33.3 | 24.9 |
| C2 | $CF_3(CF_2)_6COO^- NH_4^+$ | 68.1 | 65.0 | 54.7 | 46.1 | 29.6 | 19.8 |
| 28 | ⬡F—$CF_2OCF(CF_3)COO^-NH_4^+$ | 52.9 | 47.3 | 32.0 | 25.6 | 17.7 | 20.5 |
| C3 | $CF_3(CF_2)_3OCF(CF_3)CF_2OCF(CF_3)COO^- NH_4^+$ | 53.8 | 49.1 | 36.4 | 28.5 | 17.7 | 17.5 |
| C4 | $CF_3(CF_2)_8COO^- NH_4^+$ | 56.3 | 49.3 | 33.4 | 28.3 | 16.3 | 16.3 |
| 29 | O⬡F N$(CF_2)_2CF_2OCF(CF_3)COO^-NH_4^+$ | 41.7 | 37.5 | 25.3 | 18.7 | 18.7 | 18.5 |
| 30 | $CF_3$—⬡F—$CF_2OCF(CF_3)COO^-NH_4^+$ | 46.9 | 40.7 | 27.8 | 19.5 | 17.6 | 18.0 |

TABLE I-continued

| Example | Product tested | Surface tension (dynes/cm) | | | | | |
|---|---|---|---|---|---|---|---|
| | | 50 ppm | 100 ppm | 500 ppm | 1000 ppm | 5000 ppm | 10,000 ppm |
| 31 | —CF$_2$OCF(CF$_3$)COO$^-$NH$_4^+$ (75%) and —CF$_2$OCF(CF$_3$)CF$_2$OCF(CF$_3$)COO$^-$NH$_4^+$ (25%) | 37.4 | 32.6 | 20.4 | 18.3 | 18.1 | 18.0 |
| C5 | CF$_3$(CF$_2$)$_{10}$COO$^-$ NH$_4^+$ | 33.0 | 33.1 | 20.7 | 17.2 | 14.2 | 14.7 |
| 32 | —CF$_2$OCF(CF$_3$)CF$_2$OCF(CF$_3$)COO$^-$NH$_4^+$ | 28.1 | 24.0 | 19.9 | 20.1 | 18.5 | 18.4 |
| 33 | (CF$_3$)$_2$CF——CF$_2$OCF(CF$_3$)COO$^-$NH$_4^+$ | 33.4 | 25.4 | 18.2 | 16.2 | 17.8 | 17.1 |
| 34 | CF$_2$OCF(CF$_3$)COO$^-$NH$_4^+$ | 26.2 | 23.8 | 17.9 | 17.9 | 18.4 | 18.6 |
| 34 | —CF$_2$O[CF(CF$_3$)CF$_2$O]$_2$CF(CF$_3$)COO$^-$NH$_4^+$ | 19.7 | 19.1 | 18.6 | 18.5 | 18.3 | 18.4 |

As can be seen from the data in Table I, the perfluoro(cycloaliphatic methyleneoxyalkylene) carboxylate ammonium salts of this invention exhibit the same excellent surfactant properties as the ammonium salts of the perfluoro-α-alkoxypropionic acids or the perfluoroalkanoic acids of the same number of carbon atoms even though the ammonium salts of this invention are more highly branched than the perfluoro-α-alkoxypropionic carboxylate ammonium salts or the perfluoroalkanoic carboxylate ammonium salts.

The various modifications and alterations of this invention will be apparent to those skilled in the art without departing from the scope and spirit of this invention and this invention should not be restricted to that set forth herein for illustrative purposes.

We claim:

1. Carboxylate ammonium salt derivatives of perfluoro(cycloaliphatic methyleneoxyalkylene) compositions comprising (1) perfluoro(cycloaliphatic methyleneoxyalkylene) carbonyl fluoride compounds having (a) a perfluorocycloaliphatic moiety which can have up to two perfluoroalkyl substituents and a perfluoroalkylene substituent, and (b) a perfluoromethyleneoxyalkylene carbonyl fluoride radical, the methylene group of said radical being bonded to a ring carbon atom or said perfluoroalkylene substituent of said moiety and said alkylene group of said perfluoromethyleneoxyalkylene carbonyl fluoride being a perfluoro(methyl)methylene group, a perfluoroisopropyleneoxyperfluoro(methyl)methylene group, or a poly(perfluoroisopropyleneoxyperfluoro(methyl)-methylene group having up to about 10 perfluoroisopropyleneoxy units.

2. The compositions of claim 1 wherein said compounds can be represented by the formula $$R_fCF_2O[CFCF_2O]_nCFZ$$
$$\phantom{R_fCF_2O[}|\phantom{CFCF_2O]_n}|$$
$$\phantom{R_fCF_2O[}CF_3\phantom{CF_2O]_n}CF_3$$

wherein R$_f$ is perfluorocycloaliphatic radical

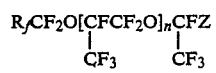,

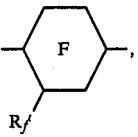

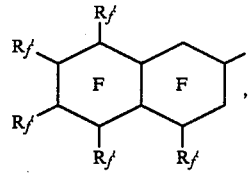

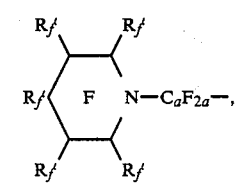

-continued

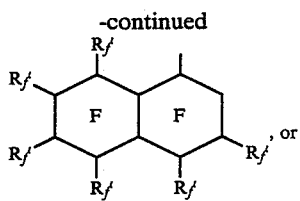, or

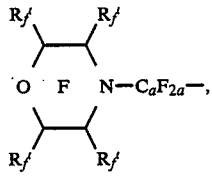

wherein
  each $R_f'$ is independently fluorine or a $C_1$ to $C_4$ straight or branched chain perfluoroalkyl radical with the proviso that no more than two $R_f'$ radicals in an $R_f$ radical are said perfluoroalkyl radicals and
  a is an integer of from 1 to 6,
  n is 0 to about 10,
  M is an ammonium radical,
  v is the valence of M.

3. A fluorochemical surfactant comprising the carboxylate ammonium salt derivative of said perfluoro(cycloaliphatic methyleneoxyalkylene) carbonyl fluoride of claim 1.

4. The fluorochemical surfactant of claim 3 wherein said carboxylate ammonium salt derivative can be represented by the formula $$R_fCF_2O[CFCF_2O]_nCFZ$$
$$\quad\quad\quad\ \ |\quad\quad\quad\ \ |$$
$$\quad\quad\quad CF_3\quad\quad\ CF_3$$

wherein $R_f$ is perfluorocycloaliphatic radical

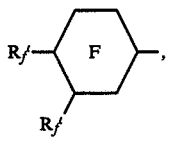,

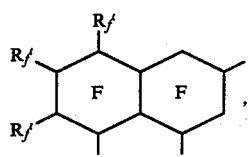,

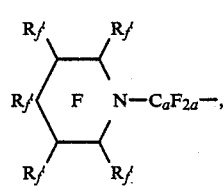,

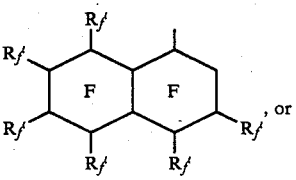, or

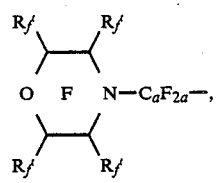, wherein
  each $R_f'$ is independently fluorine or a $C_1$ to $C_4$ straight or branched chain perfluoroalkyl radical with the proviso that no more than two $R_f'$ radicals in an $R_f$ radical are said perfluoroalkyl radicals and
  a is an integer of from 1 to 6,
  n is 0 to about 10, and
  z is $-COO^- NH_4^+$.

5. The fluorochemical surfactant of claim 3 wherein said ammonium salt derivative comprises

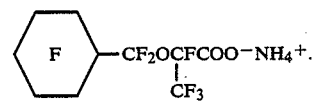

6. The fluorochemical surfactant of claim 3 wherein said ammonium salt derivative comprises

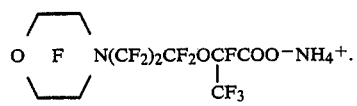

7. The fluorochemical surfactant of claim 3 wherein said ammonium salt derivative comprises

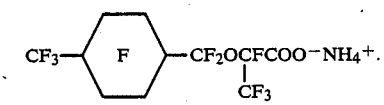

8. The fluorochemical surfactant of claim 3 wherein said ammonium salt derivative comprises

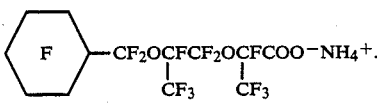

9. The fluorochemical surfactant of claim 3 wherein said ammonium salt derivative comprises

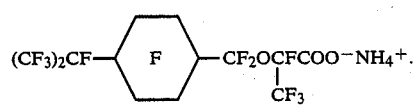

10. The fluorochemical surfactant of claim 3 wherein said ammonium salt derivative comprises

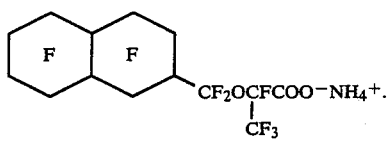
11. The fluorochemical surfactant of claim 3 wherein said ammonium salt derivative comprises
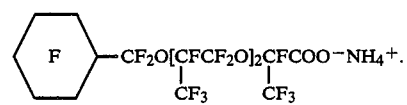
* * * * *

UNITED STATES PATENT AND TRADEMARK OFFICE
CERTIFICATE OF CORRECTION

PATENT NO. : 4,889,656
DATED : December 26, 1989
INVENTOR(S) : Richard M. Flynn, Patricia M. Savu It is certified that error appears in the above-identified patent and that said Letters Patent is hereby corrected as shown below:

Col. 7, line 51, "one" should read --once--

Col. 8, line 29, "$-CF_2O[\underset{\underset{CF_3}{|}}{C}FCF_2O]_n \underset{\underset{CF_2}{|}}{C}FCOF$"

should read -- $-CF_2O[\underset{\underset{CF_3}{|}}{C}FCF_2O]_n \underset{\underset{CF_3}{|}}{C}FCOF$ --

Col. 9, line 54, "ws" should read --was--

Col. 10, line 24, "isomer" should read --isomers--

Col. 23, line 24, after "10," insert --Z is $-COOM_{1/v'}$--

Signed and Sealed this

Thirtieth Day of April, 1991

Attest:

HARRY F. MANBECK, JR.

Attesting Officer

Commissioner of Patents and Trademarks